United States Patent [19]

Oldstone et al.

[11] Patent Number: 4,783,399

[45] Date of Patent: Nov. 8, 1988

[54] DIAGNOSTIC SYSTEM FOR THE DETECTION OF CYTOMEGALOVIRUS

[75] Inventors: Michael B. A. Oldstone, La Jolla, Calif.; George Rice, London, Canada

[73] Assignee: Scripps Clinic and Research Foundation, La Jolla, Calif.

[21] Appl. No.: 726,454

[22] Filed: Apr. 29, 1985

Related U.S. Application Data

[63] Continuation-in-part of Ser. No. 607,387, May 4, 1984.

[51] Int. Cl.$^4$ ................. G01N 33/569; G01N 33/577
[52] U.S. Cl. ............................................. 435/5; 435/7; 435/29; 435/172.2; 435/240.27; 435/810; 436/512; 436/548; 530/387; 530/808; 935/103; 935/110
[58] Field of Search ............... 435/5, 7, 172.2, 240, 435/810, 240.27; 436/512, 548, 804, 810; 935/95, 103, 110; 530/387, 808

[56] References Cited

U.S. PATENT DOCUMENTS

| | | | |
|---|---|---|---|
| 4,334,016 | 6/1982 | Furukawa | 435/5 |
| 4,444,878 | 4/1984 | Paulus | 436/512 X |

FOREIGN PATENT DOCUMENTS

0162533  11/1985  European Pat. Off. .

OTHER PUBLICATIONS

W. P. Carney et al., J. Immunol., 126 (6), 2114–2116 (Jun. 1981).
L. Pereira et al., Infect. Immun., 36 (3), 924–932 (Jun. 1982).
K. S. Kim et al., J. Clin. Microbiol., 18 (2), 331–343 (Aug. 1983).
Chemical Abstracts, 100:119064(x) (Apr. 9, 1984).
C. A. Gleaves et al., J. Clin. Microbiol., 19 (6), 917–919 (Jun. 1984).
S. H. Cheeseman et al., J. Clin. Microbiol., 20 (1), 9–44 (Jul. 1984).
N. E. Cremer et al., J. Clin. Microbiol., 21 (4), 517–521 (Apr. 1985).
Rice, G. P. A. et al., Proc. Natl. Acad. Sci., U.S.A., 81, 6134–6138 (Oct. 1984).
Schrier, R. D. et al., Science, 230, 991 and 1048–1050 (Nov. 29, 1985).
Goldstein et al., Infect. Immun., 38:273–281 (1982).
Rasmussen et al., Proc. Natl. Acad. Sci. U.S.A., 81:876–880 (1984).
Waner et al., Infect. Immun., 21:151–157 (1978).
Goding, James W., Monoclonal Antibodies: "Principles and Practice", pp. 40–46, Academic Press, N.Y., (1983).
Michelson-Fiske et al., Nature, 270:651–617 (1977).
Rinaldo et al., Transplant Proc. 8:669 (1976).
Olding et al., J. Exp. Med. 141:561 (1975).
St. Joer et al., Infect. Immun., 15:402 (1977).
Rinaldo et al., J. Immunol., 120:130–136 (1978).

Primary Examiner—Sidney Marantz
Attorney, Agent, or Firm—Dressler, Goldsmith, Shore, Sutker & Milnamow, Ltd.

[57] ABSTRACT

A mammalian monoclonal receptor is produced by a hybridoma formed by fusion of cells from a myeloma cell line and lymphocytes that produce antibodies that react with a viral antigen from a mammal immunized with cytomegalovirus-infected cells. The monoclonal receptor reacts with the viral antigen in a diagnostic system to detect the presence of cytomegalovirus in a biological sample.

44 Claims, 2 Drawing Sheets

FIG.I

DIAGNOSTIC SYSTEM FOR THE DETECTION OF CYTOMEGALOVIRUS

The Government of the United States of America has rights in the invention pursuant to grants from the National Institute of Health.

Cross-Reference to Related Application

This is a continuation-in-part application of copending application, Ser. No. 607,387, filed May 4, 1984.

Technical Field

The present invention relates to a diagnostic system for the detection of cytomegalovirus, and in particular to mammalian monoclonal antibodies that immunoreact with a viral antigen or ligand associated with cells infected by cytomegalovirus to detect the presence of cytomegalovirus in a biological sample.

Background

Cytomegalic inclusion disease (CID), generalized salivary gland virus disease, cytomegaly, and inclusion disease are synonyms for an illness caused by cytomegalovirus (CMV) infection. CMV is involved in a wide spectrum of clinical disorders from inapparent infection to severe congenital disease. Weller, T., *N. Engl. J. Med.*, 285, 203 and 267 (1971).

For example, disease occurs in patients on immunosuppressive therapy and in those subject to opportunistic infections. In fact, CMV has become the most common infection after allogeneic bone marrow transplantation and is an important determinant of the success or failure of the transplant procedure [Neiman et al., *J. Infect. Dis.*, 136, 754(1977)].

Among adults undergoing immunosuppressive therapy after renal homotransplantation, over 90 percent develop an active cytomegalovirus infection if they have cytomegalovirus antibody prior to surgery. Approximately half of the seronegative patients subsequently become infected on immunosuppressive therapy. Seronegative recipients receiving a kidney from a seropositive donor almost always develop a postoperative infection and are likely to develop symptoms.

Cytomegalovirus (CMV) infection is caused by a species-specific agent with the physio-chemical and electron microscopic characteristics of a herpesvirus. Human CMV was first isolated in fibroblastic tissue culture in the mid-1950's from infants with CID and from the adenoid tissue of schoolage children. A cytopathic effect was noted in tissue culture which was characterized by large intranuclear inclusions. The propagation of the virus provided the basis for the development of specific serologic tests as will be described.

Cytomegalovirus infection is worldwide in distribution. Cytomegalovirus, however, does not induce a highly communicable infection. Thus, a substantial number of individuals remain susceptible to the infection in adult life. CMV has been isolated from saliva, the upper respiratory tract, urine, milk, cervical secretions, semen, feces and circulating leukocytes in blood. The virus is probably transferred by intimate contact with an infected individual or by infusion of blood from a asymptomatic blood donor.

Specifically, a type of cytomegalovirus infection has been described in patients who have received blood transfusions. This condition, referred to as post-transfusion CMV mononucleosis, occurs two to four weeks after the administration of blood.

Acquired cytomegalovirus infection has also been associated with autoimmune hemolytic disease, ulcerative lesions of the gastrointestinal tract, post-transplantation pneumonia and thrombocytopenic purpura. For the majority of CMV infections acquired after birth, however, recovery is without significant complications.

The diagnosis of cytomegalovirus infection in a patient with mononucleosis-like symptoms can be established by virus isolation from vesicular lesions. Antibodies produced in response to infection with a CMV can be detected by neutralization (NT), complement-fixation (CF), immunofluorescence and platelet-agglutination (PA) procedures. [See Weller, T. H., *N. Engl. J. Med.*, 285, 203 (1971)]. Currently available serologic tests, however, must be interpreted with caution when diagnosing CMV infection because of cross-reactions with other cell-associated herpesviruses, and, for example, the tendency of CF antibody to fluctuate widely in normal subjects.

There is no satisfactory treatment for cytomegalovirus infections. The use of corticosteroids, gamma globulin and antiviral drugs such as deoxyuridine, floxuridine, cytosine arabinoside and adenine arabinoside have been reported with equivocal, beneficial, or no effect on the clinical course. But these reports are difficult to evaluate because of the small numbers of individuals treated, the multiple factors operating simultaneously and the variability of virus excretion in individuals tested at different times.

Brief Summary of the Invention

The present invention relates to mammalian monoclonal receptors, a method of preparing the receptors and diagnostics utilizing the receptors. The monoclonal receptors are produced by hybridomas formed by the fusion of cells from a myeloma cell line and splenocytes that produce antibodies that react with a viral antigen associated with cytomegalovirus.

In one aspect of the invention, a murine monoclonal receptor is produced by hybridoma ATCC HB 8554. This monoclonal receptor, designated "L-14" was formed by fusion of cells from mouse myeloma line P3X63-Ag8.653 and murine splenic cells from a mouse previously immunized with an isolate containing CMV-infected cells.

Other murine monoclonal receptors of this invention are produced by hybridomas ATCC HB 8622, ATCC HB 8623 and ATCC HB 8624. These monoclonal receptors designated "K-25", "E-28" and "A-33", respectively, were also formed by fusion of cells from mouse myeloma line P3X63-Ag8.653 and murine splenic cells from a mouse previously immunized with an isolate containing CMV-infected cells.

As demonstrated herein, monoclonal antibodies to cytomegalovirus are useful probes for studying cytomegalovirus infection, and for developing assays for measuring levels of cytomegalovirus in biological fluids and the association of such levels with disease.

In particular, one embodiment of this invention relates to a diagnostic system for assaying for the presence of a viral antigen or ligand associated with cytomegalovirus. This system includes a first package containing, as an active ingredient, an effective amount of the monoclonal antibodies of this invention. When a predetermined amount of those antibodies is admixed with a predetermined amount of a biological sample containing a particular viral antigen associated with cytomegalovirus, a complex is formed by an immunological reaction. The presence of the complex can be determined by a label or indicating means that is preferably contained in a second package of the system.

In a further aspect of the present invention, a method of preparing hybridomas that produce the above-described monoclonal receptors is contemplated. The method comprises (i) immunizing a mammal with cytomegalovirus-infected cells; (ii) removing the spleen from the mammal and making a suspension of the splenocytes or spleen cells; (iii) fusing the spleen cells with mammalian myeloma cells in the presence of a cell fusion promoter; (iv) diluting and culturing the fused cells in separate wells or containers in a medium that will not support growth of the unfused myeloma cells; (v) evaluating the supernatant in each well containing a hybridoma for the presence of a receptor to a viral antigen to cytomegalovirus; and (vi) selecting and cloning the desired hybridoma that produces a monoclonal receptor to the viral antigen.

In a still further aspect of the present invention, a method of preparing the above-described monoclonal receptors is contemplated. The method comprises culturing one of the hybridomas described herein in a suitable medium and recovering the receptor from the medium containing the hybridoma.

In yet another aspect of the present invention, a further method of preparing the abovedescribed monoclonal receptors is contemplated. The method comprises injecting into a mammal one of the hybridomas described herein and recovering the receptor from the malignant ascites or serum of the mammal.

The hybridomas and the monoclonal receptors produced therefrom described herein are identified by the designations "L-14", "K-25", "E-28" and "A-33", the particular material referred to being apparent from the context.

Hybridoma L-14 was deposited on May 2, 1984 at the American Type Culture Collection, Rockville, Md. and was given the ATCC accession number HB 8554. Hybridomas K-25, E-28 and A-33 were deposited on September 27, 1984 at the American Type Culture Collection, Rockville, Md. and were given the ATCC accession numbers HB 8622, HB 8623 and HB 8624, respectively.

The monoclonal receptors react specifically with CMV-infected cells. In particular, monoclonal receptor L-14 reacts with a protein that appears early after CMV infection (within 3 hours) and which remains localized to the cell nucleous throughout the infectious cycle. Monoclonal receptors K-25, E-28 and A-33 react with a similar specificity.

Because of the specificity of monoclonal receptors, it is possible to eliminate the problem of false positive results which would occur upon using antibodies from polyvalent human sera that are directed against viruses other than CMV.

As a result, the present monoclonal antibodies can be used to rapidly and specifically detect CMV infection in tissue culture, blood samples and other body components.

Additional advantages, benefits and uses of the present invention will become apparent to those skilled in the art from the detailed description, examples and claims which follow.

Brief Description of the Drawings

In the drawings, which constitute a portion of this disclosure:

In FIG. 1, 15 percent of the cells exhibited nuclear or perinuclear fluorescence. Similar results were obtained with a monoclonal antibody designated "E-3". [See Goldstein et al., *Infection and Immunity*, 38, 273 (1982)—the disclosure of which is incorporated herein by reference].

As shown in FIG. 2, cells from this T-lymphocyte preparation were not fluorescent when probed for late CMV viral antigen with a monoclonal antibody designated "C-5". [Goldstein et al., id.].

Detailed Description of the Invention

I. Introduction

Figure 1:
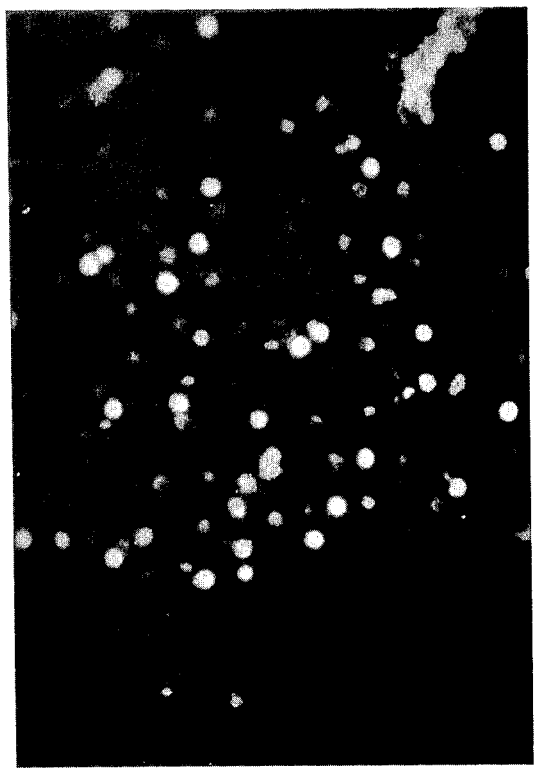
FIGS. 1 and 2 illustrate an immunofluorescence study of the reactivity of the monoclonal antibody of the present invention against a CMV isolate comprising CMV-infected cells from an adult mononucleosis patient. Peripheral blood lymphocytes (PBL) from a healthy blood donor were cultured 4 days with fibroblasts previously infected with a CMV isolate strain designated "I-G". T-lymphocytes were then isolated from the cultures by erythrocyte rosetting techniques [See Moretta et al., *J. Immunol.*, 122, 984 (1979)—the disclosure of which is incorporated herein by reference], plated onto glass slides, dried, and fixed for 10 minutes in acetone. Monocyte and B-lymphocyte contamination was less than 0.1 percent, as determined by immunofluorescence. The presence of an immediate-early viral antigen associated with CMV-infection was determined with monoclonal receptor L-14. Bound immunoglobulin was visualized with a fluorescein-conjugated goat anti-mouse immunoglobulin (Litton-Bionetics).

The term "receptor" is used herein to mean a biologically active molecule that binds to a ligand. The receptor molecules of the present invention are substantially intact antibodies or idiotype-containing polyamide portions of an antibody. Biological activity of a receptor molecule is evidenced by the binding of the receptor to its antigenic ligand upon their admixture in an aqueous medium, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polyamide portions (antibody combining sites) of antibodies are those portions of antibody molecules that include the idiotype and bind to the ligand. Such portions include the Fab, Fab' and F(ab')$_2$ fragments prepared from antibodies by well-known enzymatic cleavage techniques. See for example, U.S. Pat. No. 4,342,566 to Theofilopoulos and Dixon. Inasmuch as the antibodies from which idiotype-containing polyamides are obtained are described as raised against or induced by immunogens, idiotype-containing polyamide receptors will also be discussed as being "raised" or "induced" with the understanding that a cleavage step is required to obtain an idiotype-containing polyamide from an antibody. Intact antibodies are preferred, however, and will be utilized as illustrative of the receptor molecules of this invention.

The receptors useful on the present invention are monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monclonal antibodies of the present invention are well known. Such receptors were first described by Kohler and Milstein, Nature, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

II. Discussion

As indicated earlier, human cytomegalovirus infection is frequently associated with severe immunosuppression, especially in the clinical settings of allograft transplantation [Glenn, Rev. Infect. Dis., 3, 1151 (1981)] and acquired immunodeficiency syndrome [Stahl et al., Am. J. Med., 73, 171 (1982)]. Where the virus is harbored, how the viral genome is expressed and whether the immunosuppression is mediated directly by the virus or indirectly by another mechanism are important, but as yet, unanswered questions.

In this study, it was demonstrated that CMV can infect human peripheral blood lymphocytes (PBL) including T and B cells, natural killer cells and monocytes. The infection is best demonstrated with recent (or low passage) isolates of the virus taken from CMV-infected patients.

Further, the infection was abortive which means that expression of the CMV genome was limited to the synthesis of the immediate-early viral polypeptides or ligands, expression of late CMV gene products was not evident and infectious virus was not produced.

Lymphocytes abortively infected with CMV lost several functions, including proliferation in response to phytohemagglutinin (PHA) and the ability to perform as cytotoxic effector cells. PHA is a mitosis-stimulating substance (a mitogen) which, upon addition to a medium containing lymphocytes, prompts nondividing lymphocytes to grow, differentiate and proliferate.

Previous studies with murine CMV suggested that the virus was harbored in a latent state in a subset of murine B-lymphocytes [Olding et al., J. Exp. Med., 141, 561 (1975)]. However, until now, workers in several laboratories have failed to demonstrate a similar type of infection with human CMV.

The term "latent state" or "latent infection", as used herein, means that the virus cannot be detected in tissues or secretions by conventional cell-culture assays but nevertheless persists in a non-replicating state or at an undetectable, possibly intermittent, level of replication.

Infectious CMV has occasionally been found in buffy coat preparations [Rinaldo et al., J. Infect. Dis., 132, 421 (1975) and Jordan, Rev. Infect. Dis., 5, 205 (1983)] obtained from patients with clinical CMV infections, but the particular cell involved has not been identified. In addition, most investigators have been unsuccessful in isolating CMV from leukocyte cultures derived from healthy donors [Rinaldo et al., id. and Jordan, id.] and, until now, the replication of laboratory-adapted strains of CMV in PBL has not been convincingly demonstrated. [Rinaldo et al., J. Immunol., 120, 130 (1978) and Wahren et al., Scand. J. Immunol., 13, 581 (1981)].

If the lymphocytes were abortively infected, this would explain why techniques such as cocultivation assays and probing for late CMV gene products, would be negative. For that reason, CMV expression in PBL was investigated herein with monoclonal antibodies specifically produced to detect polypeptides relevant to the immediate-early as well as late CMV genes [Honess et al., J. Virol., 19, 231 (1974)].

Further, in light of observations of biological differences between strains of the virus (CMV isolates) recently derived from infected patients, and the fibroblast- or laboratory-adapted strains of the virus [for a review, see Weller, N. Engl. J. Med., 285, 203 (1971)] both kinds of virus were studied.

The lymphocytes employed to form the hybridomas of the present invention may be derived from any mammal, such as a primate, rodent (e.g., mouse or rat), rabbit, guinea pig, cow, dog, sheep, pig or the like. As appropriate, the host may be sensitized by injection of the immunogen, in this instance CMV-infected cells, followed by a booster injection, and then isolation of the spleen.

It is preferred that the myeloma cell line be from the same species as the lymphocytes. Therefore, fused hybrids such as mouse-mouse hybrids [Shulman et al., Nature, 276, 269 (1978)] or rat-rat hybrids [Galfre et al., Nature, 277, 131 (1979)] are typically utilized. However, some rat-mouse hybrids have also been successfully used in forming hybridomas [Goding, "Production of Monoclonal Antibodies by Cell Fusion," in Antibody as a Tool, Marchalonis et al. eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3×63 Ag8U.1 (ATCC CRL 1597), Y3-Agl.2.3. (deposited at Collection Nationale de Cultures de Microorganisms, Paris, France, number I-078) and P3×63Ag8 (ATCC TIB 9). Myeloma line P3X63-Ag8.653 is preferred for use in the present invention.

The hybridoma cells that are ultimately produced may be cultured following usual in vitro tissue culture techniques for such cells as are well-known. More preferably, the hybridoma cells are cultured in animals using similarly well-known techniques with the monoclonal receptors being obtained from the ascites fluid so generated. The animals used for generation of the ascites fluid are typically BALB/c mice bred in the mouse colony of the Scripps Clinic and Research Foundation, La Jolla, Cal., however, when animals other than mice are used for preparation of the hybridomas, mice or that animal type can be used for the production of ascites fluid.

III. Results

Peripheral blood lymphocytes (PBL) removed from the blood of healthy human donors by density gradient centrifugation on Ficoll-Pague (Sigma Chemical Co., St. Louis, Mo.) were infected at a multiplicity of 0.01 to 1.0 with CMV recently isolated from patients with various CMV syndromes (Table 1), or with stocks of plaque-purified laboratory strain AD-169. The recent isolates were propagated in human foreskin fibroblasts for less than twelve passages in RPMI-1640 medium plus 5 percent fetal calf serum. Because virus from patient isolates is predominantly associated with the cell matrix (Weller, id.), infected or mock-infected fibroblasts were sonicated, and this material was cultured with PBL for up to 4 days.

Thereafter, the PBL were washed 3 times and prepared for immunofluorescence studies by air drying and acetone fixing the cells on glass slides. After washing the slides with water, each slide was treated with a 1:50 dilution of pepsin-digested, affinity purified fluorescein-labeled, goat anti-mouse immunoglobulin (Litton-Bionetics) for thirty minutes at 4° degrees Centigrade (C.), washed with water and observed in a Zeiss microscope under phase and fluorescence microscopy. These studies revealed immediate-early, but not late, CMV viral antigens in PBL (Table 1).

isolates (Table 1). In only 1 of 8 attempts with the fibroblast-adapted, laboratory strain AD 169 (Table 1), was a weak expression of an immediate-early polypeptide demonstrated, and that occurred in less than 1 percent of PBL. Whether this represents a differential cell tropism among individual CMV strains or an adaptation of laboratory strains of virus to growth in fibroblasts, or both of these factors, is not yet clear.

A similar dichotomy among freshly isolated and laboratory-adapted strains has recently been demonstrated for another herpesvirus, Epstein-Barr virus (EBV). Sixbey et al., Nature (London), 306, 480 (1980), showed that recently isolated, but not laboratory-

TABLE 1

| | | | CMV ANTIGEN EXPRESSION[2] | |
|---|---|---|---|---|
| CMV ISOLATE[1] | SOURCE | PASSAGE NUMBER IN FIBROBLASTS | IMMEDIATE-EARLY | LATE |
| I-G | Adult CMV Mononucleosis | 12 | + | —[3] |
| I-R | Congenital CMV | 8 | + | — |
| I-B | Bone marrow transplation | 8 | + | — |
| I-P[4] | Bone marrow transplantation | 12 | — | — |
| I-S | Bone marrow transplantation | 5 | + | — |
| I-M | Congenital CMV | 8 | + | — |
| I-L | Renal transplantation | 3 | + | — |
| AD-169 | CMV Mononucleosis | 50+ | ±[5] | — |

[1]CMV isolates from patients were provided by Drs. M. Hirsch, (Massachussetts General Hospital, Boston, MA), T. Merigan, (Stanford Medical School, Stanford, CA), S. Plotkin, (Children's Hospital, Philadelphia, PA), and G. Quinnan, (Bethesda, MD). Laboratory-adapted CMV strain AD 169, isolated in 1956 by Rowe, Proc. Soc. Exp. Biol. Med., 92, 418 (1956), was obtained from the American Tissue Culture Collection in Rockville, MD [ATCC VR-538].
[2]PBL in these experiments were cultured with sonicates of virus-infected or mock-infected fibroblasts for 1 to 4 days, and then prepared for immunofluorescence studies. CMV-antigen expression was determined with murine monoclonal antibodies E-3[Goldstein et al., supra] and L-14 which are specific for immediate-early polypeptides, and C-5 [Goldstein et al., id.] which is specific to a late polypeptide. Bound immunoglobulin was probed with a pepsin-digested, affinity-purified fluorescein-labeled, goat antibody to mouse immunoglobulin, and fluorescence microscopy.
[3]"—" indicates no significant expression of the particular CMV viral antigen.
[4]CMV isolate I-P failed to induce immediate-early polypeptide synthesis in PBL in 3 of 3 experiments.
[5]Immediate-early antigen expression for laboratory-adapted CMV strain AD 169 was seen in only 1 of 8 experiments. In that experiment, fewer than 1 percent of cells were weakly positive.

Immediate-early polypeptides (viral antigens) were probed with a monoclonal antibody designated "E-3" which binds to the major 72 dalton immediate-early protein [Goldstein et al., Infection and Immunity, 38, 273 (1982)]. Similar staining was obtained with another monoclonal antibody designated "L14" which binds in infected fibroblasts to a nuclear antigen synthesized within 3 hours post infection, long before virus-induced cytopathic effect.

A monoclonal antibody designated "G-10", also specific to a CMV-induced fibroblast antigen present early in infection, did not bind to infected PBL in the same preparation. G-10 reacts with a 60 dalton protein that is synthesized in infected fibroblasts before viral cytopathic effect develops. The fine specificity of this antibody will enable a determination of the blockade in expression of the viral genome.

Typical of nonpermissive infection, the above cells did not express antigens to a monoclonal antibody designated "C-5" that is specific for a late CMV polypeptide [Goldstein et al., id.], no mature virions were visible by electron microscopy and there was no evidence of infectious virus in cocultivation assays. Thus, PBL can be infected by CMV; the infection is abortive and CMV gene expression is restricted.

As demonstrated herein, immediate-early gene expression in PBL infected with 6 of 7 low passage human adapted, strains of EBV could infect human epithelial cells and, similarly, that viral genomic expression was incomplete in infected cells.

To ascertain the subsets of PBL that CMV infects, PBL preincubated with the virus either by erythrocyte rosetting [Moretta et al., J. Immunol., 122, 984 (1979)] or with monoclonal antibody and the fluorescence activated cell sorter [Oldstone et al., Virology, 127, 426 (1983)] were separated. Two-color immunofluorescence technique [Dutko et al., J. Exp. Med., 154, 1636 (1981) and Dutko et al., J. Cell. Biochem., Supp. 8B (1984)] revealed immediate-early protein synthesis in (a) 1 to 15 percent of T-lymphocytes defined by the monoclonal antibody markers OKT3 (pan T) [ATCC CRL 8001], OKT4 (helper) [ATCC CRL 8002], OKT8 (suppressor-cytotoxic) [ATCC CRL 8014]; (b) monocytes marked by Mo2, (c) natural killer cells labeled with Leu-7 and (d) B-lymphocytes identified with antibody to surface immunoglobulin. The number of cells expressing immediate-early antigens varied with the clinical isolate used for infection.

Figure 2:
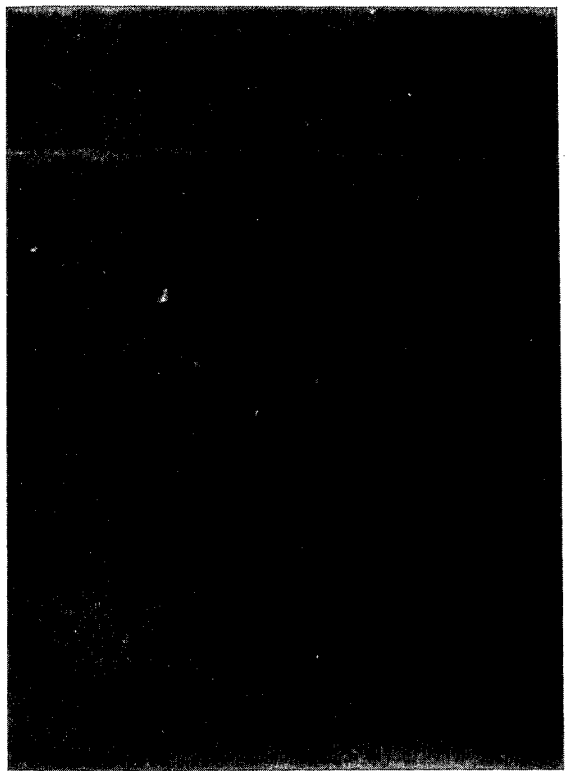

FIG. 1 illustrates CMV infected T-lymphocytes that were positively selected by rosetting techniques and then probed with the immediate-early antigen specific monoclonal antibody L-14. Similar results were obtained with the immediate-early antigen specific probe E-3, but (as shown in FIG. 2) not with C-5, a monoclonal antibody that detects a late CMV gene product.

Restricted replication of CMV with limited expression of early virus genes has recently been described for human CMV-infected mouse [La Femina et al., *J. Gen. Virol.*, 64, 373 (1983)] and rabbit cells [DeMarchi, *Virology*, 129, 274 (1983)]. Replication of murine CMV, restricted to early RNA transcripts, occurs in undifferentiated murine teratocarcinoma cells [Dutko et al., *J. Exp. Med.*, supra.]. Virus transcription in these different models may be blocked by a common mechanism, and DeMarchi has provided evidence suggesting that productive and nonproductive infection may differ at the level at which some of these early transcripts associate with polysomes [*Virology*, 129, 287 (1983)].

Whether any relevant functional deficits exist in PBL abortively infected with CMV was then examined. Such deficits would be akin to the functional aberrations in lymphocyte function that occur in vivo [Glenn, supra.; Stahl, supra and Quinnan et al., *N. Engl. J. Med.*, 307, 613 (1983)]. All the recent CMV clinical isolates that infected PBL (Table 1), suppressed (81%) the expected PHA proliferative response of PBL in repeated experiments. The data for a representative study are shown in Table 2.

TABLE 2

| SUPPRESSION OF PHA-INDUCES MITOGENESIS IN PBL CULTURED WITH VARIOUS STRAIN OF HUMAN CMV[1] | | |
|---|---|---|
| CMV ISOLATE | PASSAGE NUMBER IN FIBROBLASTS | STIMULATION INDEX[2] |
| AD 169 | 50 | 6.6 |
| I-G | 12 | 1.3 |
| Mock-Infected | N.A.[3] | 6.8 |

[1]In these studies, PBL were cultured on infected or mock-infected fibroblast monolayers for 3 days and then removed, washed and recultured in the presence of PHA (1 microgram/well) in 96-well plates ($10^5$ cells/well). After 4 days, the PBL were pulsed with tritiated thymidine (1 microcurie/well) for 24 hours and harvested; the radioactivity was then measured as described in Urbaniak et al., Handbook of Experimental Immunology, D. M. Weir (Ed.), 3.47.4 (1978).
[2]The stimulation index was determined by dividing the number of radioactive counts incorporated into PHA-stimulated PBL by the number assimilated into control cultures.
[3]Not applicable.

In contrast, the laboratory-adapted strain AD 169 and the clinical isolate I-P that failed to infect PBL were minimally suppressive (3 percent, Table 2) in the PHA assay. Lymphocyte viability, as determined by exclusion of trypan blue, was not different in mock- and virus-infected PBL.

In other studies, recent CMV isolates, but not AD 169, suppressed the ability of natural killer cells [Schrier et al., *J. Cell. Biochem.*, Supp. 8B (1984)] and virus-specific, HLA-restricted cytotoxic T-lymphocytes to lyse their appropriate targets. Thus, low passage CMV isolates can infect lymphocytes and in the process, alter their specialized functions. This observation may be important relative to CMV infection in transplant patients, considering that deficiencies in natural killer cell activity and cytotoxic T-lymphocyte responses correlate with abysmal prognosis [Quinnan et al., supra].

In conclusion, it has been demonstrated that CMV can abortively infect lymphocytes and alter some of their functions. Thus, the possibility exists that abortively infected, transfused PBL may be a source of the virus in some patients, after evolution from abortive to full replication by a mechanism that is not yet fully understood.

IV. Production of Monoclonal Receptors

Monoclonal receptor L-14, for example, was produced by immunization with a CMV isolate using the standard hybridoma technology of Kohler et al., *Nature*, 256, 495 (1975). Specifically, BALB/c mice were immunized by intraperitoneal injection with about $5 \times 10^6$ HCMV (human cytomegalovirus) AD 169-infected human fibroblast cells in complete Freund's adjuvant. Three weeks later, the mice were again injected in a like manner. After an additional three weeks, the mice were immunized intravenously with the AD 169-infected cells in phosphate buffered saline (PBS) on three consecutive days. The mice were then sacrificed.

The spleens were removed from the mice, pooled and a single cell suspension was made. The spleen cells were then fused with an equal number of P3X63-Ag8.653 myeloma cells in the presence of a cell fusion promoter (polyethylene glycol 2000). The hybridoma that produces Mab L-14 was selected by seeding the spleen cells in 96-well plates and by growth in Dulbcco's modified Eagle medium (DMEM) containing 10 percent fetal calf serum (FCS), hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against HCMV. Positive wells were cloned twice by limiting dilution. Those clones that continued to produce HCMV-specific antibody after two clonings were expanded to produce larger volumes of supernatant fluid.

Monoclonal receptors K-25, E-28 and A-33 were produced in the same manner as described above with reference to monoclonal receptor L-14.

Alternatively, the monoclonal receptors of the present invention may be produced by introducing, as by injection, the particular hybridoma into the peritoneal cavity of a mammal such as a mouse. Preferably syngenic or semi-syngenic mammals are used, as described in U.S. Pat. No. 4,361,549, the disclosure of which is incorporated herein by reference. The introduction of the hybridoma causes formation of antibody-producing hybridomas after a suitable period of growth, e.g. 1-2 weeks, and results in a high concentration of the receptor being produced that can be recovered from the bloodstream and peritoneal exudate (ascites) of the host mouse. Although the host mice also have normal receptors in their blood and ascites, the concentration of normal receptors is only about five percent that of the monoclonal receptor concentration.

The particular monoclonal receptor present in the hybridoma supernatant can be used without purification or the receptor can be recovered from the ascites or serum of the mouse using standard techniques such as affinity chromatography using AD 169-infected cells bound to an immunosorbant such Sepharose 6B or 4B (Pharmacia Fine Chemicals, Piscataway, N.J.), followed by elution from the immunosorbant using an acidic buffer such as glycine hydrochloride at a pH value of about 2.5.

V. Diagnostic Systems and Methods

As discussed previously, it is often desirable to determine if a particular antigen is present in a biological sample as an aid, for example, in the diagnosis of a particular disease.

Exemplary diagnostic reagent systems include enzyme-linked immunosorbent assays (ELISA) wherein the indicator group is an enzyme such as horseradish peroxidase that is bound to an antibody, or radioimmunoassays in which the indicating group is a radioactive element such as $^{125}I$ present in the antibody.

According to the present invention, a diagnostic system for assaying for the presence of a viral antigen associated with cytomegalovirus comprises a monoclonal antibody that immunoreacts with an admixed sample to be assayed to form an immunoreactant whose presence is signalled by an indicating means.

The indicating means can include enzyme-linked second antibodies that are raised to antibodies of the same class and from the same species of animal as the above first named antibodies. The indicating means signals the immunoreaction by binding to the first named antibodies present in the immunoreactant. In this system, the signal is indicated by the reaction of the linked enzyme with an added substrate. The indicating means can also include a radioactive element bonded to the antibodies.

The first and second antibodies, when admixed in predetermined amounts in the presence of a predetermined amount of body component or culture supernatant to be assayed, provide an amount of immunoreaction that is signalled by the indicating means. The amount of the immunoreaction is different from a known immunoreaction amount when cytomegalovirus-infected cells are not present in the body component.

Other immunochemical assay techniques suitable for use in detecting CMV-infection include at least the following three forms of enzyme immunoassay (EIA): the immunoenzymometric test, the sandwich method for antigen or antibody, and the homogeneous EIA.

The ELISA test was the first to be developed and is patterned after the standard competitive radioimmunoassay (RIA) procedure. As discussed earlier, labeled and unlabeled antigen compete for attachment to a limited quantity of solid-phase antibody. The enzyme label that is displaced is quantitated, and the calculations that follow are essentially the same as in RIA procedures.

In the immunoenzymometric procedure, an unknown quantity of antigen is reacted with an excess of enzyme-labeled antibody, and then a solid-phase antigen for the labeled antibody is added. Centrifugation removes the excess labeled antibody molecules that reacted with the solid-phase antigen, leaving enzymic activity in the soluble phase. The enzyme actively associated with the soluble phase is thereafter measured, and thereby provides a measure of the antigen concentration in the unknown sample.

The sandwich technique relies on the multivalence of antigen and its capacity to bind simultaneously with two different antibody molecules. The first antibody molecule is usually a solid-phase reactant. It is used in excess to ensure binding (complexation) of all the antigen molecules in the unknown sample. After admixture of the sample to be assayed and completion of the antigen-antibody complex-forming reaction, an excess of enzyme-labeled antibody is added and incubated with the complex resulting from the first admixture. The labeled antibody then combines with the available determinants on the antigen. Uncombined labeled antibody is removed by washing, and the enzyme activity of the bound label is determined. As before, the amount of enzyme bound to the complex is an indirect measure of the amount of antigen in the assayed sample.

Where the principal indicating group or label is an enzyme such as horseradish peroxidase (HRP) or glucose oxidase, additional reagents are required to visualize the fact that an immune reaction has occurred and the antibody-antigen complex has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-6-sulfonic acid) (ABTS).

The terms "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry.

An indicating group or label is preferably supplied along with the receptor and may be packaged therewith or packaged separately. Additional reagents such as hydrogen peroxide and diaminobenzidine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

Additional diagnostic assays can be employed to determine the presence of a CMV viral antigen. For example, CMV-infected cells can be detected by cytoplasmic staining of fixed tissue sections (immunohistology or immunofluorescence) or by use of a fluorescence-activated cell sorter (flow cytofluorometry).

Flow cytofluorometry using a fluorescence-activated cell sorter (FACS) is one method of separating T and B lymphocytes. In a FACS, droplets are generated by ultrasonic vibration in a small nozzle in such a way that each droplet contains a single cell tagged with a fluorescent label, such as FITC (fluorescein isothiocyanate) TRITC (tetramethyl rhodamine isothiocyanate). As the droplets pass one by one through a laser beam, each cell is analyzed with regard to the intensity, color and polarization of its fluorescence.

The characteristic signals from individual cells are then analyzed to determine whether the cell meets certain preselected criteria. If it does, the droplet containing the cell is electrically charged and then deflected and separated from the main stream as it passes through an electric field. By attaching appropriate fluorescent antibodies to either T or B cells, one can separate one or the other cell population from a cell suspension.

VI. Enzyme-linked Immunosorbent Assay (ELISA)

Target cells to be assayed were washed and resuspended in phosphate buffered saline (PBS) at pH 7.4, and were then plated in flat-bottom polyvinyl microtiter plates (Dynatech, Alexandria, Va.) at about $5 \times 10^4$ cells per well using 50 microliters of sample composition. The plates were then incubated overnight at 37 degrees C. in a dry oven. The dried plates were stored at 4 degrees C. until use. Prior to the ELISA assay, dried plates were rehydrated by two washes of 2 minutes each with 10 millimolar (mM) PBS, pH 7.4, containing 0.1 percent polyoxalkylene (20) sorbitan monolaurate (Tween 20) and 0.02 percent Thimerosal (sodium ethylmercurithiosalicylate), (Sigma Chemical Co., St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for 1 hour at 4 degrees C. on a gyroshaeer to contact the monoclonal antibody-containing supernatant (for example, MabL-14) with the assayed cells and to bind the receptor to its viral antigen. Following two washes of 2 minutes each, 50 microliters of peroxidase-labeled goat anti-mouse IgG+IgM (Tago, Burlingame, Calif.), diluted 1:1000, were added to each well, and the reaction mixture was incubated at 4 degrees C. for 1 hour to bind the labeled antibody to bound monoclonal antibody.

The substrate used to assay bound peroxidase activity was prepared just prior to use and consisted of 400 microgram/ml o-phenylenediamine (Sigma Chemical Co., St. Louis, Mo.) in 80 mM citrate-phosphate buffer, pH 6.0, containing 0.12 percent hydrogen peroxide. After two final washes, 50 microliters of substrate solution was added to each well and color was allowed to develop for 15 minutes in the dark. Color development was stopped by adding 25 microliters of 4 molar (M) sulfuric acid to each well and the optical absorbance at 492 nanometers (nm) was measured with a Multiskan ELISA plate reader.

VII. Indirect Immunofluorescence Assay

Unfixed tissue culture cells ($10^6$) were washed in PBS and then centrifuged in an Eppendorf centrifuge. After removing the washing fluid, the cells were resuspended in 50 microliters of Mab L-14 supernatant, for example, to contact the cells with the antibody. The cell-antibody admixture thus formed was maintained for a period of 45 minutes on ice to bind the receptors to the cells, and was then centrifuged (200 x g) through 2 ml FCS.

Thereafter, any unbound antibody and FCS were removed. The cell sediment was resuspended with 50 microliters of fluorescein-labeled goat anti-mouse antiserum diluted 1:50 (Tago, Burlingame, Calif.) and incubated another 45 minutes on ice to contact and bind the labeled anti-mouse antibodies to the bound Mab L-14 receptors. After removing any unbound second antibody as described above, the cells were fixed with 1 percent formaldehyde in PBS. Cell-bound fluorescein can be determined by using a fluorescence activated cell sorter (FACS) (Cytofluorograf, Ortho Diagnostics, Westwood, Mass.) as described earlier.

Similar results may be obtained by using monoclonal receptors K-25, E-28 and A-33.

The foregoing is intended as illustrative of the present invention but not limiting. Numerous variations and modifications may be effected without departing from true spirit and scope of the invention.

What is claimed is:

1. A mammalian monoclonal receptor produced by a hybridoma formed by fusion of cells from a myeloma line and lymphocytes that produce antibodies that react with a viral antigen induced in a mammal by a cytomegalovirus.

2. The monoclonal receptor of claim 1 wherein said mammal is a mouse.

3. The mammalian receptor of claim 1 wherein said viral antigen is an immediate-early antigen.

4. The monoclonal receptor of claim 1 which is produced by a hybridoma formed by fusion of P3×63-Ag8.653 myeloma cells and splenocytes from a BALB/c mouse previously immunized with cytomegalovirus-infected cells.

5. The monoclonal receptor of claim 4 wherein said hybridoma is hybridoma ATCC HB 8554.

6. The monoclonal receptor of claim 4 wherein said hybridoma is hybridoma ATCC HB 8622.

7. The monoclonal receptor of claim 4 wherein said hybridoma is hybridoma ATCC HB 8623.

8. The monoclonal receptor of claim 4 wherein said hybridoma is hybridoma ATCC HB 8624.

9. A diagnostic system for assaying for the presence of cytomegalovirus, said system including in at least one container as an active ingredient an effective amount of a mammalian monoclonal receptor produced by a hybridoma formed by fusion of myeloma cells and lymphocytes that produce antibodies that react with a viral antigen induced in a mammal by a cytomegalovirus.

10. The diagnostic system of claim 9 wherein said mammal is a mouse.

11. The diagnostic system of claim 9 wherein said viral antigen is an immediate-early antigen.

12. The diagnostic system of claim 11 further including an indicating group bonded to said monoclonal receptor.

13. The diagnostic system of claim 12 wherein said monoclonal receptor includes Fab fragment portions of antibodies individually bonded to said indicating group.

14. The diagnostic system of claim 9 wherein said receptor is produced by a hybridoma formed by fusion of immune murine splenocytes and P3X63-Ag8.653 myeloma cells.

15. The diagnostic system of claim 14 wherein said hybridoma is hybridoma ATCC HB 8622.

16. The diagnostic system of claim 14 wherein said hybridoma is hybridoma ATCC HB 8623.

17. The diagnostic system of claim 14 wherein said hybridoma is hybridoma ATCC HB 8624.

18. The diagnostic system of claim 9 further including an indicating group bonded to said monoclonal receptor.

19. The diagnostic system of claim 18 wherein said indicating group includes a radioactive element.

20. The diagnostic system of claim 18 wherein said indicating group includes a biologically active enzyme.

21. The diagnostic system of claim 18 wherein said monoclonal receptor includes Fab fragment portions of antibodies individually bonded to said indicating group.

22. The diagnostic system of claim 18 wherein said monoclonal receptor includes antibodies individually bonded to said indicating group.

23. A hybridoma formed by fusion of myeloma cells and lymphocytes that produce antibodies that react with a viral antigen induced in a mammal by a cytomegalovirus, which hybridoma is capable of producing a monoclonal receptor which reacts with said viral antigen.

24. The hybridoma of claim 23 wherein said mammal is a mouse.

25. The hybridoma of claim 23 which is formed by fusion of P3X63-Ag8.653 myeloma cells and immune murine splenocytes.

26. A hybridoma ATCC HB 8622 which produces a mammalian monoclonal receptor that reacts with a viral antigen induced in a mammal by a cytomegalovirus.

27. A hybridoma ATCC HB 8623 which produces a mammalian monoclonal receptor that reacts with a viral antigen induced in a mammal by a cytomegalovirus.

28. A hybridoma ATCC HB 8624 which produces a mammalian monoclonal receptor that reacts with a viral antigen induced in a mammal by a cytomegalovirus.

29. A method of preparing a hybridoma that produces a monoclonal receptor which reacts with a viral antigen to cytomegalovirus which comprises the steps of:
   (a) immunizing a mammal with cytomegalovirus-infected cells;
   (b) removing the spleen from said mammal and making a suspension of the spleen cells;
   (c) fusing said spleen cells with mammalian myeloma cells in the presence of a cell fusion promoter;
   (d) diluting and culturing the fused cells inseperate wells in a medium that will not support growth of the unfused myeloma cells;
   (e) evaluating the supernatant in each well containing a hybridoma for the presence of a receptor to a viral antigen to cytomegalovirus;
   (f) selecting and cloning a hybridoma producing the receptor that reacts with the viral antigen; and
   (g) recovering the hybridoma that produces a monoclonal receptor of step (f), above.

30. A method of preparing a mammalian monoclonal receptor that reacts with a viral antigen to cytomegalovirus, which comprises culturing the hybridoma ATCC HB 8622 in a medium and recovering the receptor from medium containing the hybridoma.

31. The method of claim 30 wherein said hybridoma is introduced into the peritoneal cavity of a host mammal, growing said hybridoma in said host mammal, and recovering the receptor from the malignant ascites or serum of said mammal.

32. A method of preparing a mammalian monoclonal receptor that reacts with a viral antigen to cytomegalovirus, which comprises culturing the hybridoma ATCC HB 8623 in a medium and recovering the receptor from medium containing the hybridoma.

33. The method of claim 32 wherein said hybridoma is introduced into the peritoneal cavity of a host mammal, growing said hybridoma in said host mammal, and recovering the receptor from the malignant ascites or serum of said mammal.

34. A method of preparing a mammalian monoclonal receptor that reacts with a viral antigen to cytomegalovirus, which comprises culturing the hybridoma ATCC HB 8624 in a medium and recovering the receptor from medium containing the hybridoma.

35. The method of claim 34 wherein said hybridoma is introduced into the peritoneal cavity of a host mammal, growing said hybridoma in said host mammal, and recovering the receptor from the malignant ascites or serum of said mammal.

36. A method for assaying human peripheral blood lymphocytes for a cytomegalovrius immediate-early antigen comprising the steps of:
   (a) providing a sample of peripheral blood lymphocytes to be assayed;
   (b) contacting said peripheral blood lymphocytes with receptor molecules that immunoreact with said immediate-early antigen and are produced by a hybridoma having an ATCC accession number selected from the group consisting of HB 8622, HB 8623 and HB 8624;
   (c) maintaining said contact for a time sufficient for said receptor molecules to immunologically bind to immediate-early cytomegalovirus antigen present in said sample and form an immunoreactant; and
   (d) assaying for the presence of said immunoreactant and thereby the presence of said cytomegalovirus immediate-early antigen.

37. The method of claim 36 wherein said immediate-early antigen is a perinuclear protein.

38. The method of claim 36 wherein said immediate-early antigen is a nuclear protein.

39. The method of claim 36 wherein said receptor molecule is an intact antibody molecule.

40. The method of claim 36 wherein said peripheral blood lymphocytes are B-lymphocytes.

41. The method of claim 36 wherein said peripheral blood lymphocytes are T-lymphocytes.

42. The method of claim 41 wherein said T-lymphocytes are OKT3 positive.

43. The method of claim 41 wherein said T-lymphocytes are OKT4 positive.

44. The method of claim 41 wherein said T-lymphocytes are OKT8 positive.

* * * * *

UNITED STATES PATENT AND TRADEMARK OFFICE
CERTIFICATE OF CORRECTION

PATENT NO. : 4,783,399
DATED : November 8, 1988
INVENTOR(S) : Michael B. A. Oldstone and George Rice It is certified that error appears in the above-identified patent and that said Letters Patent is hereby corrected as shown below:

Column 1,
Line 5, insert:

-- This invention was made with government support under Grant Nos. AI 07007, NS 12428, AI 21640 and CA 35048 from the National Institutes of Health. The U.S. government may have certain rights in the invention. --

Signed and Sealed this

Fourth Day of June, 2002

Attest:

JAMES E. ROGAN
Attesting Officer    Director of the United States Patent and Trademark Office